(12) United States Patent
Heuler et al.

(10) Patent No.: US 12,146,834 B2
(45) Date of Patent: Nov. 19, 2024

(54) SYSTEMS AND METHODS FOR DETECTION OF CHOCOLATE BLOOM

(71) Applicant: University of South Florida, Tampa, FL (US)

(72) Inventors: Joshua Stewart Heuler, Lutz, FL (US); Siyu He, New York City, NY (US); Sharad Ambardar, Tampa, FL (US); Dmitri V. Voronin, Tampa, FL (US)

(73) Assignee: University of South Florida, Tampa, FL (US)

( * ) Notice: Subject to any disclaimer, the term of this patent is extended or adjusted under 35 U.S.C. 154(b) by 335 days.

(21) Appl. No.: 17/682,578

(22) Filed: Feb. 28, 2022

(65) Prior Publication Data

US 2022/0276172 A1  Sep. 1, 2022

Related U.S. Application Data

(60) Provisional application No. 63/154,994, filed on Mar. 1, 2021.

(51) Int. Cl.
| | |
|---|---|
| *G01N 21/65* | (2006.01) |
| *A23G 1/00* | (2006.01) |
| *A23G 1/50* | (2006.01) |
| *G01N 33/02* | (2006.01) |

(52) U.S. Cl.
CPC ........... *G01N 21/65* (2013.01); *A23G 1/0006* (2013.01); *A23G 1/50* (2013.01); *G01N 33/02* (2013.01); *G01N 2201/06113* (2013.01)

(58) Field of Classification Search
None
See application file for complete search history.

(56) References Cited

U.S. PATENT DOCUMENTS

| | | | |
|---|---|---|---|
| 4,847,105 | A | 7/1989 | Yokobori |
| 5,849,353 | A | 12/1998 | Baker et al. |
| 5,925,399 | A | 7/1999 | Cheng et al. |
| 8,545,921 | B2 | 10/2013 | Gonus et al. |
| 2018/0146693 | A2 | 5/2018 | Bjarne |

FOREIGN PATENT DOCUMENTS

WO  WO-2012079800 A1 *  6/2012  ........... G01N 23/201

OTHER PUBLICATIONS

Heuler, et al., "Point-of-care detection, characterization, and removal of chocolate bloom using a handheld Raman spectrometer", Scientific Reports | (2020) 10:9833 | https://doi.org/10.1038/s41598-020-66820-1.

* cited by examiner

*Primary Examiner* — Jyoti Chawla
(74) *Attorney, Agent, or Firm* — Meunier Carlin & Curfman LLC

(57) ABSTRACT

In an embodiment, a bloom engine is created that can detect the formation of both fat bloom and sugar bloom in a chocolate product. A Raman spectrometer is used to generate a first or reference spectrum of a chocolate product. Based on peaks of the spectrum known to be associated with sugar and peaks of the spectrum known to be associated with fat, a ratio of sugar to fat for the chocolate product is determined based on the reference spectrum. Later, a second spectrum is generated from the chocolate product, and a ratio of sugar to fat is similarly determined for the second spectrum. Changes in the ratios between the two samples are used to detect fat or sugar bloom. Other features of the bloom engine including removing or reducing bloom from the chocolate product using a laser associated with the spectrometer and applying a design to the chocolate product in bloom using the laser.

20 Claims, 5 Drawing Sheets

200

300

400

SYSTEMS AND METHODS FOR DETECTION OF CHOCOLATE BLOOM

CROSS-REFERENCE TO RELATED APPLICATIONS

This application claims priority to U.S. Provisional Patent Application No. 63/154,994, filed on Mar. 1, 2021, and entitled "SYSTEMS AND METHODS FOR DETECTION OF CHOCOLATE BLOOM." The disclosure of which is hereby incorporated by reference in its entirety.

BACKGROUND

The main components of milk and dark chocolate include cocoa solids, cocoa butter, and sugar, with milk chocolate containing additional milk solids. The distribution of ingredients in the cocoa butter matrix combined with the crystalline structure of the cocoa are the key determinants of the characteristics of chocolate products. Cocoa butter has six crystalline forms (polymorphs) numbered according to their thermal stability, with polymorph VI being the most stable. Polymorph V is preferred by chocolate manufacturers because it gives chocolate its desirable qualities. The challenge for a chocolate maker is to ensure that their chocolate contains polymorph V when it reaches consumers.

One of the greatest limitations on the shelf-life and overall quality of chocolate is the formation of chocolate bloom. Chocolate bloom is an off-white coating on the surface of chocolate products due to the altered distribution of the ingredients. Bloom reduces the shelf-life of chocolate and affects its visual and tactile quality, all of which are serious concerns for chocolate manufacturers and consumers. Chocolate bloom can take on a uniform or a marbled appearance, and the resulting beige appearance on the surface of the milk or dark chocolate is viewed by consumers as an indicator of poor quality. Bloom is classified as fat bloom or sugar bloom based on the chemical composition. However, a combination of both sugar bloom and fat bloom in the same sample has been observed.

Chocolate bloom can be caused by flaws in the chocolate composition (such as fatty fillings), manufacturing errors (such as poor tempering), and improper storage in warm and/or humid conditions. The presence of polymorph VI instead of the polymorph V found in unbloomed chocolate is the main chemical indication of the fat bloom. When chocolate is heated, the cocoa butter polymorphs separate and recrystallize at the surface. Cracks in the chocolate from cooling may accelerate the process. Polymorph VI resists melting during temperature fluctuations, which is thought to produce bloom seed crystals for molten cocoa butter to crystallize around upon cooling.

Sugar bloom is caused by a different process. The diffusion of the cocoa alters the distribution of the chocolate ingredients and can trap sugar crystals at the surface. Sugar bloom can also be caused by moisture dissolving sugar and forming crystals at the surface of the chocolate. Either bloom formation renders the product unappealing for consumers and manufacturers.

Detecting and characterizing chocolate bloom rapidly and inexpensively is a serious challenge for the chocolate industry. For example, annual production of more than 3.5 million metric tons of chocolate by over 2000 companies involving over 200,000 people in Europe has been reported, with over 90% of which were small and medium sized enterprises producing chocolates containing fillings, such as hazelnuts, almonds, macadamia nuts, and others. The complex heterogeneous composition of pure and filled chocolate products, and a variety of manufacturing conditions lead to a large diversity of the causes of chocolate bloom. In particular, the filled chocolate products are especially susceptible to fat bloom formation via complex oil migration mechanisms. The formation of chocolate bloom at the industrial level could happen during the manufacturing and packaging stages and may be due to the variations in the ambient conditions such as temperature and moisture, as well as the chemical compositions of the heterogeneous chocolate products, various fillings, and tempering conditions. Continuous monitoring and quality control of those parameters has been a challenge.

SUMMARY

In an embodiment, a bloom engine is created that can detect the formation of both fat bloom and sugar bloom in a chocolate product. A Raman spectrometer is used to generate a first or reference spectrum of a chocolate product. Based on peaks of the spectrum known to be associated with sugar and peaks of the spectrum known to be associated with fat, a ratio of sugar to fat for the chocolate product is determined from the reference spectrum. Later, a second spectrum is generated from the chocolate product, and a ratio of sugar to fat is similarly determined for the second spectrum. Changes in the ratios between the two samples are used to detect fat or sugar bloom. Other features of the bloom engine including removing or reducing bloom from the chocolate product using a laser associated with the spectrometer and applying a design to the chocolate product in bloom using the laser.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The foregoing summary, as well as the following detailed description of illustrative embodiments, is better understood when read in conjunction with the appended drawings. For the purpose of illustrating the embodiments, there is shown in the drawings example constructions of the embodiments; however, the embodiments are not limited to the specific methods and instrumentalities disclosed. In the drawings.

DETAILED DESCRIPTION

Figure 1:
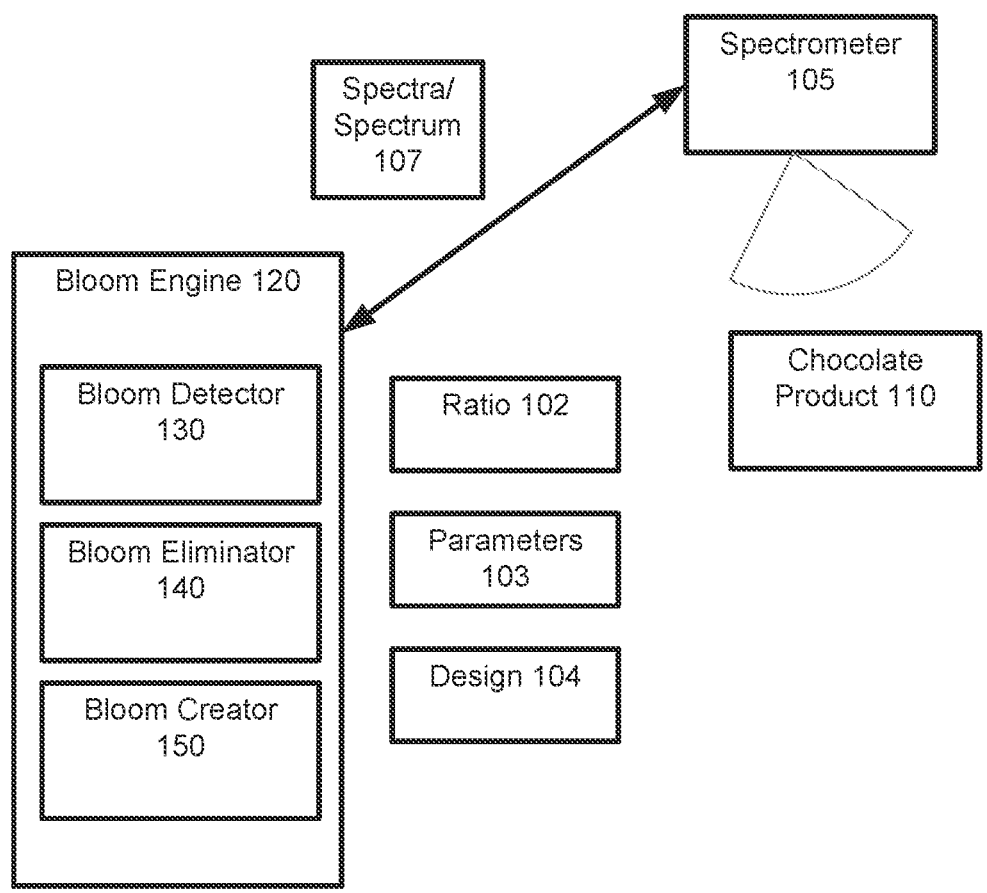
FIG. 1 is an illustration of an environment for detecting and reducing chocolate bloom in chocolate products.

FIG. 1 is an environment 100 for detecting and eliminating bloom. As shown the environment 100 include a bloom engine 120 in communication with a spectrometer 105. The spectrometer 105 may be a laser spectrometer including a handheld Raman spectrometer. Other types of spectrometers may be used.

The spectrometer 105 may be used to generate and provide a spectrum 107 related to a chocolate product 110 to the bloom engine 120. As will be described further below, the bloom engine 120 may use the generated spectrum 107 to detect both sugar bloom and fat bloom in the chocolate product 110. In addition, the bloom engine 120 may be used to remove bloom from a chocolate product 110, or may be used to cause bloom to form on a chocolate product 110. For example, the bloom engine 120 may use the spectrometer 105 (or other laser) to purposely create bloom on the chocolate product 110 to form a desired design or text.

Sugar bloom in a chocolate product occurs when moisture comes into contact with a chocolate product 10. The moisture dissolves at least some of the sugar in the chocolate product 110. When the moisture evaporates it leaves behind small sugar crystals on the surface of the chocolate product 110. These small crystals are evidence of sugar bloom.

Fat bloom occurs when some of the fat or cocoa butter melts and separates from the chocolate product 110. This fat may then rise to the surface of the chocolate product 110 where it solidifies as a grayish solid which is evidence of fat bloom. Fat bloom may occur when the chocolate has been exposed to heat.

As shown, the bloom engine 120 includes several components including, but not limited to, a bloom detector 130, a bloom eliminator 140, and a bloom creator 150. More or fewer components may be supported. The bloom engine 120, and the components 130, 140, and 150, may be implemented together or separately using one or more general purpose computing devices such as the computing system 500 illustrated with respect to FIG. 5.

The bloom detector 130 may detect bloom in one or more chocolate products 110. In particular, the bloom detector 130 may use the spectrometer 105 to periodically measure peaks of fats and sugars in chocolate products 110 at various stages of the manufacturing process including manufacturing, shipping, and storage. The measurements may be used as feedback during the manufacturing process and may be used to detect or prevent the formation of bloom. In one embodiment, a ratio 102 of the peaks of fats to sugars in a chocolate product 110 may be used to detect the formation of bloom.

In one embodiment, a handheld spectrometer 105 is used to take measurements (i.e., spectra 107) of a chocolate product 110 in various stages of the manufacturing process. Each spectrum 107 may include peaks known to be associated with sugar and peaks known to be associated with fats. For example, sugar may be associated with peaks in the spectrum at 403 cm$^{-1}$. Fat, such as cocoa butter and other oils used in the chocolate product 110, may be associated with peaks such as 1439 cm-1 to 1464 cm-1 and 1298 cm$^{-1}$. This and another fats band at 1298 cm-1.

The bloom detector 130 may determine the area under the peaks associated with sugar and the area under the peaks associated with fats. The bloom detector 130 may use the determined areas to calculate a ratio of sugar to fat (i.e., the ratio 102).

The bloom detector 130 may use the calculated ratios 102 to detect the occurrence of sugar or fat bloom in a chocolate product 110. At a first time, the bloom detector 130 may use the spectrometer 105 to generate a first spectrum 107 from a first region of the chocolate product 110. The bloom detector 130 may then calculate the ratio 102 for the first sample. The first sample may also be referred to as a reference sample. At a later second time, the bloom detector 130 may use the spectrometer 105 to generate a second spectrum 107 from a second region of the chocolate product 110. The bloom detector 130 may then calculate the ratio 102 for the second sample. Depending on the embodiments, the first and second regions may be the same or different locations on the outside of a same or different chocolate product 110.

The bloom detector 130 may compare the first ratio 102 taken at the first time with the ratio taken at the second time to detect sugar or chocolate bloom in the sample. In particular, an increase in the ratio 102 may indicate that there is more sugar on the surface of the chocolate product 110 at the second time than the first time, which is a characteristic of sugar bloom. On the other hand, a decrease in the ratio 102 may indicate that there is more fat on the surface of the chocolate product 110 at the second time than the first time, which is a characteristic of fat bloom. The amount of change in the ratio 102 between the first and second times may indicate the severity of the sugar or fat bloom.

The bloom detector 130 may be used to identify possible causes of bloom in the manufacturing process associated with a chocolate product 110 such as a candy bar. For example, spectra 107 may be collected from a chocolate product 110 at various stages of the manufacturing process including logistics chain such as when the chocolate product 110 is created, when the chocolate products 110 is packaged, when the chocolate product 110 waits for shipping, when the chocolate product 110 is shipped, when the chocolate product 110 arrives at a retailer warehouse, and when the product arrives at a relater location for sale to the general public.

The bloom detector 130 may use the spectra 107 collected at each stage to generate a ratio 102 of sugar and fat for the chocolate product 110 at each stage. Based on the ratios 102, the bloom detector 130 may identify stages most associated with increases in fat or sugar bloom. For example, the bloom detector 130 may determine based on a comparison of a ratio 102 computed after the chocolate product 110 is received at the retailer warehouse and a ratio 102 computed before the chocolate product 110 was shipped to the retailer warehouse, that fat blooming occurred during the shipment to the retailer warehouse. In response, the bloom detector 130 may recommend that the temperature of the chocolate be reduced or better controlled during shipment.

As another example, the bloom detector 130 may determine based on a comparison of a ratio 102 computed after the chocolate product 110 is packaged and a ratio 102 computed after the chocolate product 110 is manufactured, that sugar blooming occurred between the time the sample was manufactured and packaged. In response, the bloom detector 130 may recommend that moisture levels be better controlled where the chocolate product 110 is placed after manufacturing.

The bloom eliminator 140 may be used to remove or reduce bloom from a chocolate product 110. Where the spectrometer 105 is a laser spectrometer 105, the spectrometer 105 may be capable of generating focused heat in a region of a chocolate product 110. As may be appreciated, because bloom is associated with a separation of either sugar or fat from the chocolate product 110, applying heat to a region of the chocolate sample 110 where bloom was detected may cause the separated sugar or fat, along with the chocolate in the region, to melt together. Depending on the time and intensity of the applied heat, the melted chocolate and separated sugar or fat in the region may solidify together resulting in a reduction of bloom in the region of the chocolate product 110. Note that lasers other than the laser associated with the spectrometer 105 may be used for bloom removal.

In some embodiments, the bloom eliminator 140 may receive chocolate product 110 having a region associated with bloom. The bloom may be sugar bloom, fat bloom, or some combination of both. The bloom in the region of the chocolate product 110 may have been determined by the bloom detector 130 using the spectrometer 105 or may have been visually determined by an observer.

The bloom eliminator 140 may determine a ratio 102 for the region associated with bloom. The bloom eliminator 140 may then cause the spectrometer 105 to apply a laser at or around the location of the region associated with bloom. The time that the laser is applied (i.e., exposure), as well as the power and wavelength of the laser, may be selected by a user or administrator. The exposure, wavelength, and power are referred to herein as the parameters 103. In some embodiments, the parameters 103 may be selected based on the color of the chocolate, the extent or severity of the bloom, and the type of bloom (i.e., sugar or fat bloom).

In some embodiments, after the region of the chocolate product 110 is treated for bloom and allowed to cool, the bloom eliminator 140 may generate a ratio 102 for the region of the chocolate product 110. The bloom eliminator 140 may compare the ratio 102 generated before the bloom removal with the ratio 102 generated after the bloom removal. Depending on whether or how much the ratio 102 has improved, indicating a reduction of bloom, the bloom eliminator 140 may repeat the bloom eliminating process with the spectrometer 105 (or other laser) using the same or adjusted parameters 103.

The bloom creator 150 may purposely create bloom on the surface of a chocolate product 110 according to a design 104. The design 104 may include graphics designs, textual designs, or some combination thereof. Similar to how the bloom eliminator 140 uses a laser of the spectrometer 105 to reduce bloom in regions of the chocolate product 110 where bloom is detected, the bloom creator 150 may use the laser of the spectrometer 105 to induce or create bloom in regions of the chocolate product 110 for the purposes of etching or drawing the design 104 into the surface of the chocolate product 110.

Previously, most designs were applied to chocolate products using specialized dyes or inks or using lasers or other tools that engraved the design into the chocolate. A drawback associated with such engraving is that it requires that some amount of chocolate be removed from the product due to the engraving. In contrast, applying a design 104 to the surface of the chocolate product 110 using bloom requires no removal of chocolate from the chocolate product 110.

In some embodiments, the bloom creator 150 may select parameters 103 for the laser of the spectrometer 105 to use during the application of the design 104 based on a variety of factors such as the desired amount of bloom to use for the design 104, and the color or type of the chocolate product 110. For example, the whiteness of the resulting bloom may increase with increased exposure or power, and darker chocolate products 110 may require a higher exposure or power to achieve the same color or shade of bloom.

In some embodiments, the bloom creator 150 may receive a design 104 from a user or administrator and may control the spectrometer 105 to create bloom on the chocolate product 110 corresponding to the received design 105. The design 104 may be provided as a raster or vector image file. Depending on the embodiment, the bloom creator 150 may expose a graphical user interface through which a user or administrator may create a design 104 for the chocolate product 110.

Figure 2:
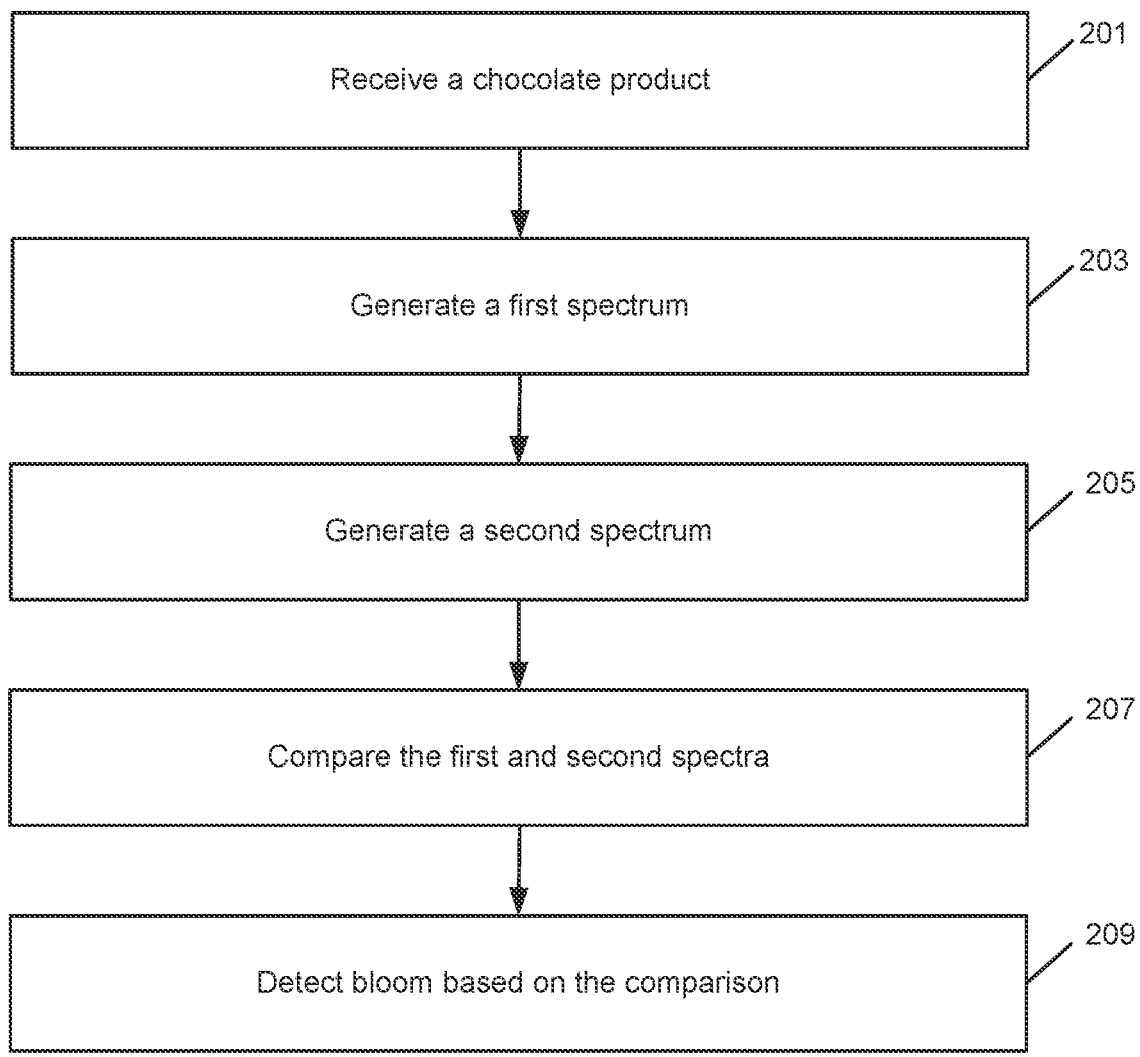
FIG. 2 is an illustration of an example method for detecting bloom in a chocolate product.

FIG. 2 is an illustration of an example method 200 for detecting bloom in a chocolate sample 110. The method 200 may be implemented in part by a spectrometer 105 and the bloom engine 120.

At 201, a chocolate product is received. The chocolate product 110 may be received from a factory or after having been transported to a location such as a retailer. For example, the chocolate product 110 may be randomly selected from a set of chocolate products 110 coming off of a manufacturing line, from a set of chocolate products 110 waiting to be loaded onto a truck for delivery, or from a set of chocolate products 110 that were transported to a retailer.

At 203, a first spectrum is generated. The first spectrum 107 may be generated by the spectrometer 105 and may be associated with a first region of the chocolate product 110. The first region may be a region of the chocolate product 110 that is not associated with bloom. The first spectrum 107 may be a reference spectrum 107 and may include one or more peaks associated with sugar and one or more peaks associated with fat. The first spectrum 107 may be generated by the spectrometer 107 according to one or more parameters 103 such as laser wavelength, power, and exposure.

At 205, a second spectrum is generated. The second spectrum 107 may be generated by the spectrometer 105 and maybe associated with a second region of the chocolate product 110. The second region of the chocolate product may be different than the first region and may be a region where a user or administrator desires to determine if there is bloom. The bloom may include both sugar bloom and fat bloom.

At 207, the first and second spectra are compared. The first and second spectra may be compared by calculating a first ratio 102 of fat peaks and sugar peaks from the first spectrum 107 and calculating a second ratio 102 of fat peaks and sugar peaks from the second spectrum 107. The first ratio 102 may be considered as a reference ratio 102 that represents the ratio of fat peaks to sugar peaks (or vice versa) that would be expected in a region of the chocolate product 110 where no bloom is present.

At 209, bloom is detected in the second region based on the comparison. Depending on the embodiment. if the second ratio 102 is different than the first ratio 102 it may indicate that there is bloom in the second region. Whether the second ratio is higher or lower than the first ratio may further indicate whether the bloom is fat bloom or sugar bloom. Note that the bloom may be detected in the region even where the bloom is not yet visible to a human observer.

In some embodiments, upon detecting the bloom, one or more remedial actions may be taken. If the chocolate product 110 is received from an assembly line or manufacturing process, upon detecting the bloom, the manufacturer may adjust one or more parameters associated with the manufacturing of the chocolate product 110 such as temperature, humidity, ingredient ratios, mixing times, etc. If the chocolate product 110 is received from a storage location or shipping provider, upon detecting the bloom, the manufacturer may adjust one or more parameters associated with the transportation or storage of the chocolate product such as temperature, humidity, time, etc.

Figure 3:
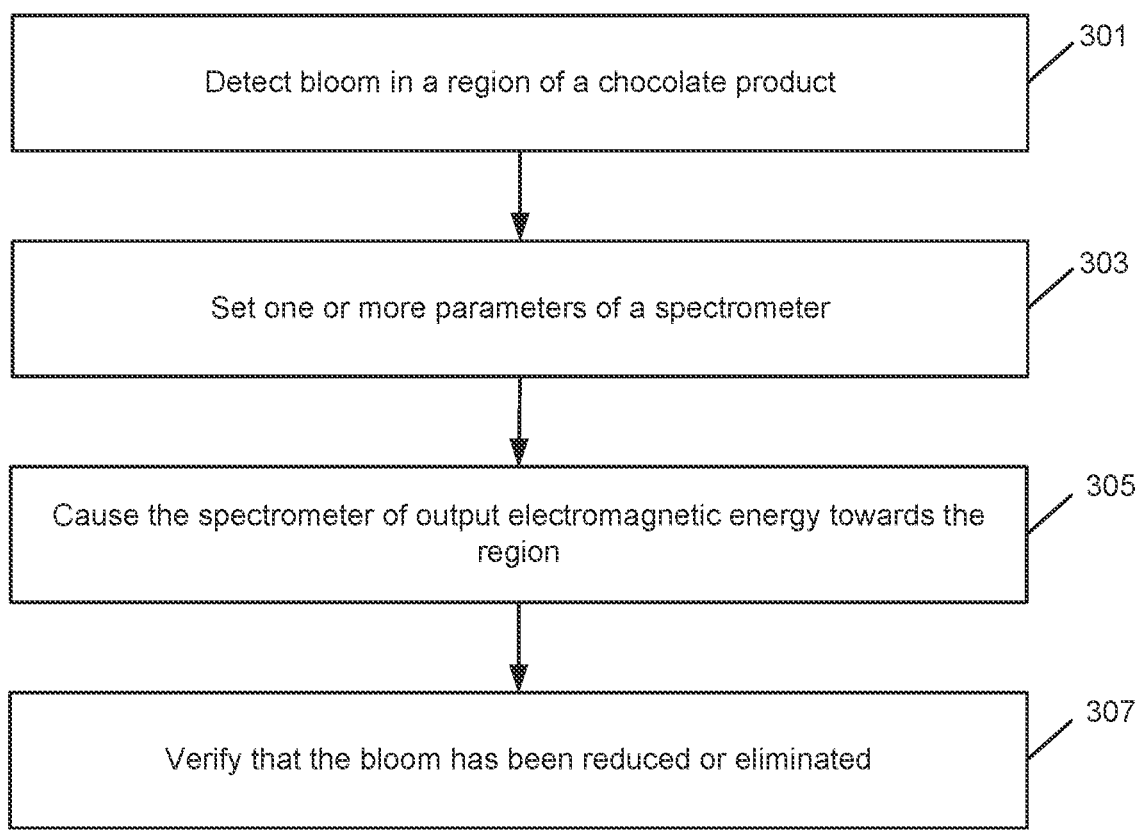
FIG. 3 is an illustration of an example method for removing bloom from a chocolate product.

FIG. 3 is an illustration of an example method 300 for removing bloom. The method 300 may be implemented in part by a spectrometer 105 and the bloom engine 120.

At 301, bloom is detected in a region of a chocolate product 110. The bloom may be detected using a spectrometer 105 and the method 200 of FIG. 2.

At 303, one or more parameters of the spectrometer are set. The parameters 103 may include wavelength, power, and exposure. The parameters 103 may be set such that the output of the spectrometer laser is sufficient to reduce or remove the detected bloom from the chocolate product 110. The parameters 103 may depend on the color or darkness of the chocolate product 110 and the ingredients of the chocolate product 110, for example.

At 305, the spectrometer is caused to output electromagnetic energy towards the region. The spectrometer 105 may be caused to output electromagnetic energy by an operator of the spectrometer 105 or the bloom eliminator 140. Depending on the embodiment, the spectrometer 105 may be a Raman handheld spectrometer 105. Other types of spectrometers 105 may be used. Note that the electromagnetic energy may be output by a laser other than the laser associated with the spectrometer 105.

At 307, that the bloom has been reduced or eliminated is verified. Depending on the embodiment, the operator may verify that the bloom is no longer visible or has a reduced visibility. Alternatively, the operator may test the region for bloom using the method 200 of FIG. 2.

Figure 4:
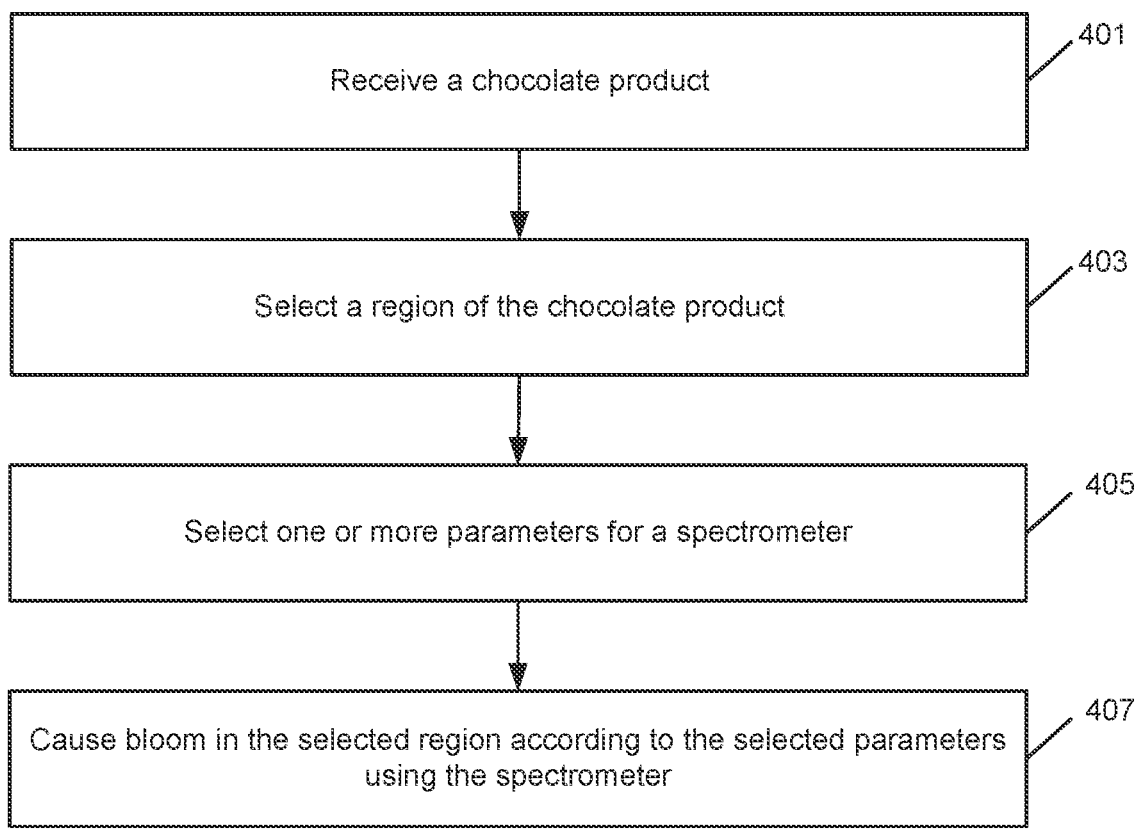
FIG. 4 is an illustration of an example method for causing bloom in a chocolate product.

FIG. 4 is an illustration of an example method 400 for causing bloom in a chocolate product 110. The method 400 may be implemented in part by a spectrometer 105 and the bloom creator 150.

At 401, a chocolate product is received. The chocolate product 110 may be received by the bloom creator 150. The chocolate product 110 may have been selected so that a user or administrator can cause bloom on one or more surface regions of the chocolate product 110. As may be appreciated, bloom on a region of a chocolate product 110 results in a lightening of the region that is related to the amount of bloom. Accordingly, a design 104 may be incorporated onto a chocolate product 110 by causing bloom at various intensities to form on the surface of the chocolate product 110.

At 403, a region of the chocolate product is selected. The region may be selected by the bloom detector 130. The region may correspond to a part or aspect of the design 104 that is being placed on the chocolate product 110 using bloom.

At 405, one or more parameters for a spectrometer are selected. The parameters 103 may be selected by the bloom creator 150. The parameters 103 may include power, wavelength, and exposure. The parameters may be selected based on a variety of factors such as the amount of bloom desired and the color of the chocolate product.

At 407, bloom is caused in the selected region according to the selected parameters using the spectrometer. The bloom may be caused by the bloom creator 150 using the spectrometer 105 or another laser not associated with the spectrometer 105. After causing the bloom, the method 400 may return to 403 where another region of the chocolate product 110 is selected for bloom application.

Figure 5:
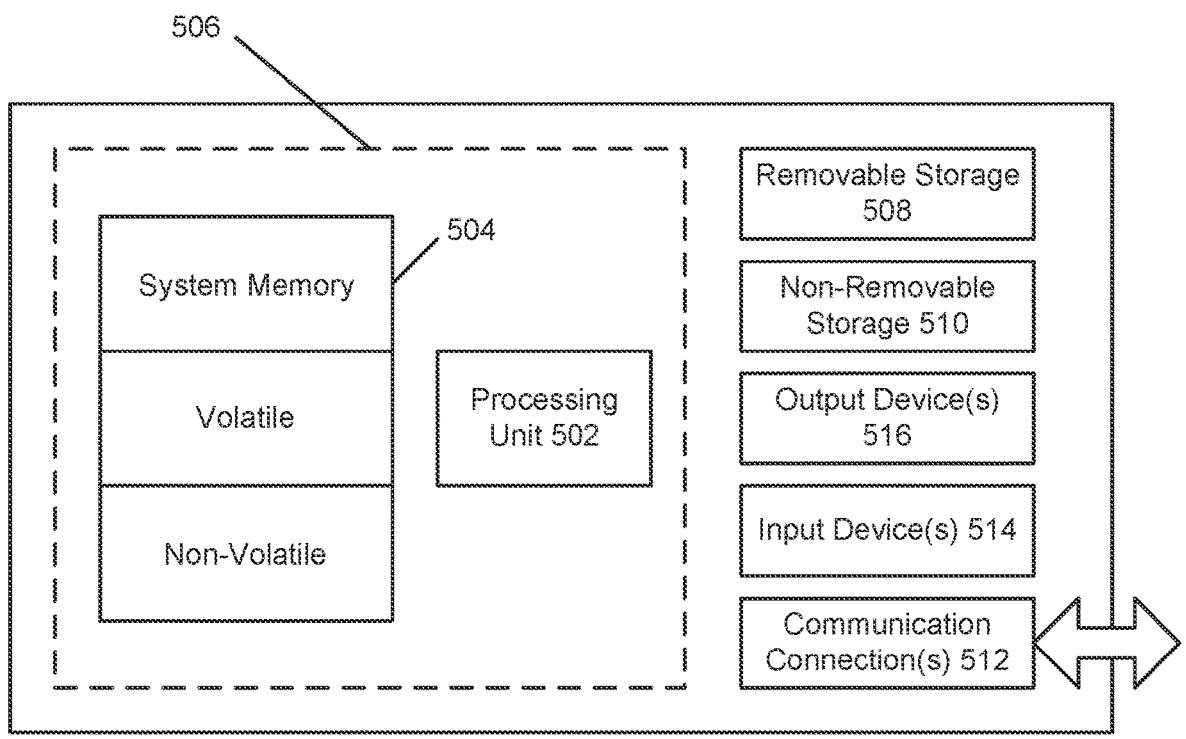
FIG. 5 shows an exemplary computing environment in which example embodiments and aspects may be implemented.

FIG. 5 shows an exemplary computing environment in which example embodiments and aspects may be implemented. The computing device environment is only one example of a suitable computing environment and is not intended to suggest any limitation as to the scope of use or functionality.

Numerous other general purpose or special purpose computing devices environments or configurations may be used. Examples of well-known computing devices, environments, and/or configurations that may be suitable for use include, but are not limited to, personal computers, server computers, handheld or laptop devices, multiprocessor systems, microprocessor-based systems, network personal computers (PCs), minicomputers, mainframe computers, embedded systems, distributed computing environments that include any of the above systems or devices, and the like.

Computer-executable instructions, such as program modules, being executed by a computer may be used. Generally, program modules include routines, programs, objects, components, data structures, etc. that perform particular tasks or implement particular abstract data types. Distributed computing environments may be used where tasks are performed by remote processing devices that are linked through a communications network or other data transmission medium. In a distributed computing environment, program modules and other data may be located in both local and remote computer storage media including memory storage devices.

With reference to FIG. 5, an exemplary system for implementing aspects described herein includes a computing device, such as computing device 500. In its most basic configuration, computing device 500 typically includes at least one processing unit 502 and memory 504. Depending on the exact configuration and type of computing device, memory 504 may be volatile (such as random access memory (RAM)), non-volatile (such as read-only memory (ROM), flash memory, etc.), or some combination of the two. This most basic configuration is illustrated in FIG. 5 by dashed line 506.

Computing device 500 may have additional features/functionality. For example, computing device 500 may include additional storage (removable and/or non-removable) including, but not limited to, magnetic or optical disks or tape. Such additional storage is illustrated in FIG. 5 by removable storage 508 and non-removable storage 510.

Computing device 500 typically includes a variety of computer readable media. Computer readable media can be any available media that can be accessed by the device 500 and includes both volatile and non-volatile media, removable and non-removable media.

Computer storage media include volatile and non-volatile, and removable and non-removable media implemented in any method or technology for storage of information such as computer readable instructions, data structures, program modules or other data. Memory 504, removable storage 508, and non-removable storage 510 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 500. Any such computer storage media may be part of computing device 500.

Computing device 500 may contain communication connection(s) 512 that allow the device to communicate with other devices. Computing device 500 may also have input device(s) 514 such as a keyboard, mouse, pen, voice input device, touch input device, etc. Output device(s) 516 such as a display, speakers, printer, etc. may also be included. All these devices are well known in the art and need not be discussed at length here.

It should be understood that the various techniques described herein may be implemented in connection with hardware components or software components or, where appropriate, with a combination of both. Illustrative types of hardware components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc. The methods and apparatus of the presently disclosed subject matter, or certain aspects or portions thereof, may take the form of program code (i.e., instructions) embodied in tangible media, such as floppy diskettes, CD-ROMs, hard drives, or any other machine-readable storage medium where, when the program code is loaded into and executed by a machine, such as a computer, the machine becomes an apparatus for practicing the presently disclosed subject matter.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A method for detecting bloom on a chocolate product, the method comprising:
   receiving a chocolate product;
   generating a first spectrum of the chocolate product in a first region of the chocolate product by a computing device;
   generating a second spectrum of the chocolate product in a second region of the chocolate product by the computing device;
   comparing the first spectrum with the second spectrum by the computing device; and
   detecting bloom in the second region based on the comparison by the computing device.

2. The method of claim 1, further comprising:
   determining a first ratio of a sugar peak and a fat peak in the first spectrum; and
   determining a second ratio of the sugar peak and the fat peak in the second spectrum.

3. The method of claim 2, wherein comparing the first spectrum with the second spectrum comprises comparing the first ratio with the second ratio.

4. The method of claim 3, wherein detecting bloom in the second region based on the comparison comprises detecting bloom based on the comparison between the first ratio and the second ratio.

5. The method of claim 1, wherein the bloom comprises sugar bloom or fat bloom.

6. The method of claim 1, wherein the first spectrum is generated by a handheld spectrometer.

7. The method of claim 1, further comprising adjusting one or more of a manufacturing process or a transportation process associated with the chocolate product in response to detecting the bloom.

8. The method of claim 1, further comprising setting one or more parameters of a spectrometer prior to generating the first spectrum.

9. The method of claim 8, wherein the one or more parameters comprise laser power, laser wavelength, and exposure.

10. The method of claim 9, wherein the wavelength is approximately 1064 nm.

11. The method of claim 9, wherein the laser power is approximately 300 mW.

12. The method of claim 9, wherein the exposure is approximately 5 seconds.

13. A method for bloom removal on a chocolate product:
    detecting bloom on a region of a chocolate product by a computing device;
    setting one or more parameters of a spectrometer by the computing device;
    causing the spectrometer to output electromagnetic energy towards the region of the chocolate product by the computing device; and
    verifying that the bloom has been reduced or eliminated in the region of the chocolate product by the computing device.

14. The method of claim 13, wherein the bloom is detected using the spectrometer.

15. The method of claim 13, wherein the bloom is fat bloom.

16. The method of claim 13, wherein the parameters comprise one or more of power, wavelength, and exposure.

17. The method of claim 13, wherein spectrometer is a handheld Raman spectrometer.

18. A method for inducing bloom in a chocolate product:
    receiving a chocolate product;
    selecting a region of the chocolate product;
    selecting one or more parameters for a spectrometer; and
    causing bloom in the selected region of the chocolate product according to the selected parameters using the spectrometer.

19. The method of claim 18, wherein the one or more parameters comprise one or more of power, wavelength, and exposure.

20. The method of claim 19, wherein selecting the one or more parameters comprises selecting the one or more parameters according to a desired color for the region.

* * * * *